United States Patent [19]

Rivier et al.

[11] Patent Number: 4,563,352

[45] Date of Patent: * Jan. 7, 1986

[54] HUMAN PANCREATIC GRF

[75] Inventors: Jean E. F. Rivier, La Jolla; Joachim Spiess, Encinitas; Wylie W. Vale, Jr., La Jolla, all of Calif.

[73] Assignee: The Salk Institute For Biological Studies, San Diego, Calif.

[ * ] Notice: The portion of the term of this patent subsequent to May 14, 2002 has been disclaimed.

[21] Appl. No.: 432,663

[22] Filed: Oct. 4, 1982

[51] Int. Cl.$^4$ ..................... C07C 103/52; A61K 37/02
[52] U.S. Cl. ................................. 514/12; 260/112.5 R
[58] Field of Search .................. 260/112.5 R; 424/177

[56] References Cited

U.S. PATENT DOCUMENTS 4,218,474  8/1980  Barnish et al. ..................... 424/177

OTHER PUBLICATIONS

Esch et al., *Biochemical and Biophysical Research Communications*, 109, No. 1, 152–158 (1982).
Esch et al., *The Journal of Biological Chemistry*, 258, No. 3, 1806–1812 (1983).
Li et al., *J. Am. Chem. Soc.*, 92:26 (1970) pp. 7608–7609.
Veber et al., *Biochem. & Biophys. Res. Commun.*, 45, No. 1, 235–9 (1971).
Frohman et al., *Clin. Invest.*, 65, 43–54 (1980).
Spiess et al., *Biochemistry*, vol. 21, 1982, pp. 6037–6040.
Spiess et al., *Nature*, vol. 303, 1983, pp. 532–535.
Tharner et al., *The Lancet*, Jan. 1/8, 1983, pp. 24–28.
Rivier et al., *8th American Peptide Symposium*, May 22–27, 1983, Tucson, Arizona, p. 237.
Spiess et al., *Biochemistry*, 21, 6037–6040 (1982).
Spiess et al., *Nature*, 303 (9), 532–535 (1983).
Tharner et al., *The Lancet*, No. 831415, 24–28 (1983).

*Primary Examiner*—Delbert R. Phillips
*Assistant Examiner*—F. T. Moezic
*Attorney, Agent, or Firm*—Fitch, Even, Tabin & Flannery

[57] ABSTRACT

Human pancreatic GRF has been synthesized. The invention provides synthetic peptides which are extremely potent in stimulating the release of pituitary GH in mammals and which have the formula: H-Tyr-Ala-Asp-Ala-Ile-Phe-Thr-Asn-Ser-Tyr-Arg-Lys-Val-Leu-$R_{15}$-Gln-Leu-Ser-Ala-Arg-Lys-Leu-Leu-Gln-Asp-Ile-Met-Ser-Arg-Gln-Gln-Gly-Glu-Ser-Asn-Gln-Glu-Arg-Gly-$R_{40}$-$R_{41}$-$R_{42}$-Y wherein $R_{15}$ is Gly or D-Ala, $R_{40}$ is Ala or des-$R_{40}$, $R_{41}$ is Phe or des-$R_{41}$, $R_{42}$ is des-$R_{42}$ or 1 to 8 different amino acid residues selected from the group consisting of Gln, Gly, Ile, Leu, Lys, Pro, Thr and Val, and Y signifies the carboxyl moiety of the amino acid residue at the C-terminal and is the radical -COOR$_1$,-CR$_1$O,-CONHNHR$_1$,-CON(R$_1$)(R$_2$) or -CH$_2$OR$_1$, with R$_1$ and R$_2$ being lower alkyl or hydrogen. These peptides or biologically active fragments thereof, or analogs thereof having well-known substitutions and/or additions, as well as nontoxic salts of any of the foregoing, may be administered therapeutically to animals, including humans, and may be used diagnostically.

13 Claims, No Drawings

HUMAN PANCREATIC GRF

This invention was made with Government support under Grant No. AM-26741 awarded by the National Institutes of Health. The Government has certain rights in this invention.

The present invention relates to a peptide having influence on the function of the pituitary gland in humans and other animals, particularly mammals. In particular, the present invention is directed to a peptide which promotes the release of growth hormone by the pituitary gland.

BACKGROUND OF THE INVENTION

Physiologists have long recognized that the hypothalamus controls all the secretory functions of the adenohypophysis with the hypothalamus producing special polypeptides which trigger the secretion of each pituitary hormone. A hypothalamic releasing factor has been characterized for the pituitary hormones thyrotropin and prolactin (the tripeptide TRF), for the pituitary gonadotropins luteinizing hormone and follicle stimulating hormone (the decapeptide LRF, LH-RH or GnRH) and for the pituitary hormones $\beta$-endorphin and adrenocorticotropin (the 41-amino acid polypeptide CRF). An inhibitory factor has also been characterized in the form of somatostatin which inhibits the secretion of growth hormone (GH). Each of these hypothalamic releasing factors and somatostatin have been reproduced by total synthesis, and analogs of the native structures have been synthesized.

A corresponding hypothalamic releasing factor for the pituitary GH has long been sought after.

SUMMARY OF THE INVENTION

A polypeptide has been isolated from an extract from a human pancreatic tumor, purified, characterized, synthesized and tested which promotes the release of GH by the pituitary. The sequence of the first 40 residues of this peptide is as follows: Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Glu-Ser-Asn-Gln-Glu-Arg-Gly-Ala. The peptide is believed to be and is hereinafter referred to as hpGRF (for human pancreatic tumor GH releasing factor).

Pharmaceutical compositions in accordance with the invention include hpGRF, or an analog or a biologically active fragment thereof, or a nontoxic salt of the foregoing, dispersed in a pharmaceutically acceptable liquid or solid carrier. Such pharmaceutical compositions can be used in clinical medicine, both human and veterinary, for administration for therapeutic purposes, and also diagnostically.

DETAILED DESCRIPTION OF PREFERRED EMBODIMENTS

The nomenclature used to define the peptides is that specified by Schroder & Lubke, "The Peptides", Academic Press (1965), wherein in accordance with conventional representation the amino group at the N-terminal appears to the left and the carboxyl group at the C-terminal to the right. Where the amino acid residue has isomeric forms, it is the L-form of the amino acid that is represented unless otherwise expressly indicated.

The invention provides synthetic hpGRF peptides having the following formula: H-Tyr-Ala-Asp-Ala-Ile-Phe-Thr-Asn-Ser-Tyr-Arg-Lys-Val-Leu-$R_{15}$-Gln-Leu-Ser-Ala-Arg-Lys-Leu-Leu-Gln-Asp-Ile-Met-Ser-Arg-Gln-Gln-Gly-Glu-Ser-Asn-Gln-Glu-Arg-Gly-$R_{40}$-$R_{41}$-$R_{42}$-Y wherein $R_{15}$ is Gly or D-Ala, $R_{40}$ is Ala or des-$R_{40}$, $R_{41}$ is Phe or des-$R_{41}$, $R_{42}$ is des-$R_{42}$ or 1 to 8 different amino acid residues selected from the group consisting of Gln, Gly, Ile, Leu, Lys, Pro, Thr and Val, and Y signifies the carboxyl moiety of the amino acid residue at the C-terminal and is the radical —COOR$_1$, —CR$_1$O, —CONHNHR$_1$, —CON(R$_1$)(R$_2$) or —CH$_2$OR$_1$, with R$_1$ and R$_2$ being lower alkyl or hydrogen. Methyl, ethyl and propyl are the preferred lower alkyl groups. Fragments of foregoing peptides also have biological potency.

The peptides are synthesized by a suitable method, such as by exclusively solid-phase techniques, by partial solid-phase techniques, by fragment condensation, by classical solution couplings, or by the employment of recently developed recombinant DNA techniques. For example, the techniques of exclusively solid-phase synthesis are set forth in the textbook "Solid-Phase Peptide Synthesis", Stewart & Young, Freeman & Co., San Francisco, 1969, and are exemplified by the disclosure of U.S. Pat. No. 4,105,603, issued Aug. 8, 1978 to Vale et al. The fragment condensation method of synthesis is exemplified in U.S. Pat. No. 3,972,859 (Aug. 3, 1976). Other available syntheses are exemplified by U.S. Pat. No. 3,842,067 (Oct. 15, 1974) and U.S. Pat. No. 3,862,925 (Jan. 28, 1975).

Common to such syntheses is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with side-chain protecting groups linked to the appropriate residues.

Also considered to be within the scope of the present invention are intermediates of the formula: $X^1$-Tyr($X^2$)-Ala-Asp($X^3$)-Ala-Ile-Phe-Thr($X^4$)-Asn($X^5$)-Ser($X^4$)-Tyr($X^2$)-Arg($X^6$)-Lys($X^7$)-Val-Leu-$R_{15}$-Gln($X^5$)-Leu-Ser($X^4$)-Ala-Arg($X^6$)-Lys($X^7$)-Leu-Leu-Gln($X^5$)-Asp($X^3$)-Ile-Met-Ser($X^4$)-Arg($X^6$)-Gln($X^5$)-Gln($X^5$)-Gly-Glu($X^3$)-Ser($X^4$)-Asn($X^5$)-Gln($X^5$)-Glu($X^3$)-Arg($X^6$)-Gly-$R_{40}$-$R_{41}$-$R_{42}$-$X^8$ wherein: $X^1$ is either hydrogen or an $\alpha$-amino protecting group. The $\alpha$-amino protecting groups contemplated by $X^1$ are those known to be useful in the art of step-wise synthesis of polypeptides. Among the classes of $\alpha$-amino protecting groups covered by $X^1$ are (1) acyl-type protecting groups, such as formyl, trifluoroacetyl, phthalyl, toluenesulfonyl(Tos), benzensulfonyl, nitrophenylsulfenyl, tritylsulfenyl, o-nitrophenoxyacetyl, chloroacetyl, acetyl, and $\gamma$-chlorobutyryl; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethyloxycarbonyl, isopropyloxycarbonyl, ethoxycarbonyl, allyloxycarbonyl; (4) cycloalkyl urethan-type protecting groups, such as cyclopentyloxycarbonyl, adamantyloxycarbonyl,and cyclohexyloxycarbonyl; (5) thiourethan-type protecting groups, such as phenylthiocarbonyl; (6) alkyl-type protecting groups, such as triphenylmethyl (trityl), benzyl; (7) trialkylsilane groups, such as trimethylsilane. The preferred α-amino protecting group is BOC.

$X^2$ is a protecting group for the phenolic hydroxyl group of Tyr selected from the group consisting of tetrahydropyranyl, tert-butyl, trityl, Bzl, CBZ, 4Br-CBZ and 2,6-dichlorobenzyl (DCB). The preferred protecting group is 2,6-dichlorobenzyl. $X^2$ can be hydrogen which means that there is no protecting group on the hydroxyl group.

$X^3$ is hydrogen or an ester-forming protecting group for the carboxyl group of Asp or Glu and is selected from the group consisting of benzyl (OBzl), 2,6-dichlorobenzyl, methyl and ethyl.

$X^4$ is a protecting group for the hydroxyl group of Thr or Ser and is selected from the group consisting of acetyl, benzoyl, tert-butyl, trityl, tetrahydropyranyl, Bzl, 2,6-dichlorobenzyl and CBZ. The preferred protecting group is Bzl. $X^4$ can be hydrogen, which means there is no protecting group on the hydroxyl group.

$X^5$ is hydrogen or a protecting group for the side chain amido group of Asn or Gln, and it is preferably xanthyl(Xan).

$X^6$ is a protecting group for the guanidino group of Arg selected from the group consisting of nitro, Tos, CBZ, adamantyloxycarbonyl, and BOC, or is hydrogen;

$X^7$ is hydrogen or a protecting group for the side chain amino substituent of Lys. Illustrative of suitable side chain amino protecting groups are 2-chlorobenzyloxycarbonyl (2-Cl-Z), Tos, t-amyloxycarbonyl and BOC.

Met can optionally be protected by oxygen, but is preferably left unprotected.

The selection of a side chain amino protecting group is not critical except that it must be one which is not removed during deprotection of the α-amino groups during the synthesis. Hence, the α-amino protecting group and the side chain amino protecting group should not be the same.

$X^8$ can be a protecting group for the C-terminal carboxyl group, such as the ester-forming group $X^3$, or an anchoring bond used in solid-phase synthesis for linking to a solid resin support, or is des-$X^8$, in which case the residue at the C-terminal has a carboxyl moiety which is Y. When a solid resin support is used, it may have the formulae: —O—CH$_2$-resin support, —O—CH$_2$-benzyl-polyamide resin support, —NH-benzhydrylamine (BHA) resin support, and —NH-paramethylbenzhydrylamine (MBHA) resin support. The polyamide polymer is commercially available and is discussed in detail in *Bioorganic Chemistry*, 8, 351–370 (1979) where a preferred version of it is discussed in connection with the synthesis illustrated in FIG. 6. When it is employed, the side-chain-protecting groups may first be cleaved by hydrogen fluoride (HF) treatment, and the peptide may subsequently be cleaved from the resin as the amide by ammonolysis. When the unsubstituted amide is desired, use of BHA or MBHA resin is preferred, because cleavage directly gives the amide. In case the N-methyl amide is desired, it can be generated from an N-methyl BHA resin.

In the formula for the intermediate, at least one of the X-groups is a protecting group or $X^8$ includes resin support.

In selecting a particular side chain protecting group to be used in the synthesis of the peptides, the following rules are followed: (a) the protecting group must retain its protecting properties and not be split off under coupling conditions, (b) the protecting group should be stable to the reagent and, with the exception of Xan, should be stable under the reaction conditions selected for removing the α-amino protecting group at each step of the synthesis, and (c) the side chain protecting group must be removable, upon the completion of the synthesis containing the desired amino acid sequence, under reaction conditions that will not alter the peptide chain.

The peptides are preferably prepared using solid phase synthesis, such as that described by Merrifield, *J. Am. Chem. Soc.*, 85, p 2149 (1963), although other equivalent chemical syntheses known in the art can also be used as previously mentioned. Solid-phase synthesis is commenced from the C-terminal end of the peptide by coupling a protected α-amino acid to a suitable resin. Such a starting material can be prepared by attaching α-amino-protected Ala by an ester linkage to a chloromethylated resin or a hydroxymethyl resin, or by an amide bond to a BHA resin or MBHA resin. The preparation of the hydroxymethyl resin is described by Bodansky et al., *Chem. Ind.* (London) 38, 1597–98 (1966). Chloromethylated resins are commercially available from Bio Rad Laboratories, Richmond, Calif. and from Lab. Systems, Inc. The preparation of such a resin is described by Stewart et al., "Solid Phase Peptide Synthesis" (Freeman & Co., San Francisco 1969), Chapter 1, pp 1–6. BHA and MBHA resin supports are commercially available and are generally used only when the desired polypeptide being synthesized has an unsubstituted amide at the C-terminal. If a methyl, ethyl or propylamide is to be incorporated in the resulting polypeptide, a chloromethylated or hydroxymethyl resin is used, and cleavage is suitably effected by using the appropriate amine, e.g. ethylamine.

Ala, protected by BOC, can be coupled to the chloromethylated resin according to the procedure of Monahan and Gilon, Biopolymer 12, pp 2513–19, 1973. Following the coupling of BOC-Ala to the resin support, the α-amino protecting group is removed, as by using trifluoroacetic acid(TFA) in methylene chloride, TFA alone or HCl in dioxane. The deprotection is carried out at a temperature between about 0° C. and room temperature. Other standard cleaving reagents and conditions for removal of specific α-amino protecting groups may be used as described in Schroder & Lubke, "The Peptides", 1 pp 72–75 (Academic Press 1965).

After removal of the α-amino protecting group of Phe, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. The selection of an appropriate coupling reagent is within the skill of the art. Particularly suitable as a coupling reagent is N,N'-dicyclohexyl carbodiimide (DCCI).

The activating reagents used in the solid phase synthesis of the peptides are well known in the peptide art. Examples of suitable activating reagents are carbodiimides, such as N,N'-diisopropyl carbodiimide, N-ethyl- N'-(3-dimethylaminopropyl)carbodiimide. Other activating reagents and their use in peptide coupling are described by Schroder & Lubke supra, in Chapter III and by Kapoor, *J. Phar. Sci.,* 59, pp 1-27 (1970).

Each protected amino acid or amino acid sequence is introduced into the solid phase reactor in about a fourfold or more excess, and the coupling may be carried out in a medium of dimethylformamide(DMF):CH$_2$Cl$_2$ (1:1) or in DMF or CH$_2$Cl$_2$ alone. In cases where incomplete coupling occurs, the coupling procedure is repeated before removal of the α-amino protecting group prior to the coupling of the next amino acid. The success of the coupling reaction at each stage of the synthesis is monitored by the ninhydrin reaction, as described by E. Kaiser et al., *Anal. Biochem.* 34, 595 (1970). The coupling reactions can be performed automatically, as on a Beckman 990 automatic synthesizer, using a program such as that reported in Rivier et al. *Biopolymers,* 1978, 17, pp 1927-1938.

After the desired amino acid sequence has been completed, the intermediate peptide can be removed from the resin support by treatment with a reagent, such as liquid hydrogen fluoride, which not only cleaves the peptide from the resin but also cleaves all remaining side chain protecting groups $X^2$, $X^3$, $X^4$, $X^5$, $X^6$ and $X^7$, the anchoring bond $X^8$ and the α-amino protecting group $X^1$, to obtain the peptide in the form of the free acid. Should the ethylamide, for example, be desired, the peptide can be cleaved by treatment with dry ethylamine. Because Met is present in the sequence, the BOC protecting group is preferably first cleaved using trifluoroacetic acid (TFA)/ethanedithiol prior to cleaving the peptide from the resin with HF to eliminate potential S-alkylation. When using hydrogen fluoride for cleaving, anisole and methylethyl sulfide are included in the reaction vessel for scavenging.

The following Example sets forth the preferred method for synthesizing hpGRF by the solid-phase technique. It will of course be appreciated that the synthesis of a correspondingly shorter peptide fragment is effected in the same manner by merely eliminating the requisite number of amino acids at either end of the chain; however, it is presently felt that biologically active fragments should contain the indicated sequence at the N-terminal.

EXAMPLE I

The synthesis of hpGRF(1-40)-NH$_2$ having the formula: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Glu-Ser-Asn-Gln-Glu-Arg-Gly-Ala-NH$_2$ is conducted in a stepwise manner using a Beckman 990 peptide synthesizer on a MBHA hydrochloride resin, such as that available from Bachem, Inc., having a substitution range of about 0.1 to 0.5 mmoles/g. resin. Coupling of BOC-Ala to the resin is performed by the general procedure set forth below in Schedules A and B which is used throughout the synthesis, and it results in the substitution of about 0.35 mmol. Ala per gram of resin. All solvents that are used are carefully degassed by sparging with an inert gas, e.g. helium or nitrogen, to insure the absence of oxygen that might undesirably oxidize the sulfur of the Met residue.

After deblocking and neutralization, the peptide chain is built step-by-step on the resin. Deblocking, neutralization and addition of each amino acid is performed in general accordance with the procedure set forth in detail in Vale et al. U.S. Pat. No. 4,292,313.

Deblocking is preferably carried out in accordance with Schedule A which follows:

SCHEDULE A

| Reagent | Mixing time (Min.) |
| --- | --- |
| 1. 60% TFA/2% ethanedithiol | 10 |
| 2. 60% TFA/2% ethanedithiol | 15 |
| 3. IPA/1% ethanedithiol | 0.5 |
| 4. Et$_3$N (10%) in CH$_2$Cl$_2$ | 0.5 |
| 5. MeOH | 0.5 |
| 6. Et$_3$N (10%) in CH$_2$Cl$_2$ | 0.5 |
| 7. MeOH (twice) | 0.5 |
| 8. CH$_2$Cl$_2$ (twice) | 0.5 |

The couplings are preferably carried out as set out in Schedule B which follows:

SCHEDULE B

| Reagent | Mixing time (Min.) |
| --- | --- |
| 9. DCCI | — |
| 10. Boc-amino acid | 50-90 |
| 11. MeOH (twice) | 0.5 |
| 12. CH$_2$Cl$_2$ (twice) | 0.5 |
| 13. Ac$_2$O (3 M) in CH$_2$Cl$_2$ | 15.0 |
| 14. CH$_2$Cl$_2$ | 0.5 |
| 15. MeOH | 0.5 |
| 16. CH$_2$Cl$_2$ (twice) | 0.5 |

Briefly, one to two mmol. of BOC-protected amino acid in methylene chloride is used per gram of resin, plus one equivalent of 1.0 molar DCCI in methylene chloride for two hours. When BOC-Arg(TOS) is being coupled, a mixture of 50% DMF and methylene chloride is used. Bzl ether is used as the hydroxyl side-chain protecting group for Ser and Thr. P-nitrophenyl ester-(ONp) is used to activate the carboxyl end of Asn or Gln, and for example, BOC-Asn(ONp) is coupled overnight using one equivalent of HOBt in a 50% mixture of DMF and methylene chloride, in which case no DCC is added. The amido group of Asn or Gln is protected by Xan when DCC coupling is used instead of the active ester method. 2-chlorobenzyloxycarbonyl (2Cl-Z) is used as the protecting group for the Lys side chain. Tos is used to protect the guanidino group of Arg, and the Glu or Asp carboxyl group is protected as the Bzl ester (OBzl). The phenolic hydroxyl group of Tyr is protected with 2,6-dichlorobenzyl (DCB). At the end of the synthesis, the following composition is obtained: $X^1$-Tyr($X^2$)-Ala-Asp($X^3$)-Ala-Ile-Phe-Thr($X^4$)-Asn($X^5$)-Ser($X^4$)-Tyr($X^2$)-Arg($X^6$)-Lys($X^7$)-Val-Leu-Gly-Gln($X^5$)-Leu-Ser($X^4$)-Ala-Arg($X^6$)-Lys($X^7$)-Leu-Leu-Gln($X^5$)-Asp($X^3$)-Ile-Met-Ser($X^4$)-Arg($X^6$)-Gln($X^5$)-Gln($X^5$)-Gly-Glu($X^3$)-Ser($X^5$)-Asn($X^5$)-Gln($X^5$)-Glu($X^3$)-Arg($X^6$)-Gly-Ala-$X^8$ wherein $X^1$ is BOC, $X^2$ is DCB, $X^3$ is benzyl ester, $X^4$ is Bzl, $X^5$ is Xan, $X^6$ is Tos, $X^7$ is 2Cl-Z and $X^8$ is -NH-resin support. Xan may have been partially or totally removed by TFA treatment used to deblock the α-amino protecting group.

After the final Tyr residue has been coupled to the resin, BOC is removed with 60% TFA in CH$_2$Cl$_2$. In order to cleave and deprotect the remaining protected peptide-resin, it is treated with 1.5 ml. anisole, 0.5 ml. methylethylsulfide and 15 ml. hydrogen fluoride (HF) per gram of peptide-resin, at −20° C. for one-half hour and at 0.° C. for one-half hour. After elimination of the HF under high vacuum, the resin-peptide remainder is washed alternately with dry diethyl ether and chloroform, and the peptide is then extracted with degassed 2N aqueous acetic acid and separated from the resin by filtration.

The cleaved and deprotected peptide is then dissolved in 0–5% acetic acid and subjected to purification which may include Sephadex G-50 fine gel filtration.

The peptide is then further purified by preparative or semi-preparative HPLC as described in Rivier et al., *Peptides: Structure and Biological Function*, (1979) pp 125-8 and Marki et al. *J. Am. Chem. Soc.* 103, 3178 (1981). In summary, cartridges fitting Waters Associates prep LC-500 are packed with 15–20μ $C_{18}$ Silica from Vydac (300 Å). A gradient of $CH_3CN$ in TEAP is generated by a low pressure Eldex gradient maker, as described in Rivier, J., *J. Liq. Chromatography* 1, 343–367 (1978). The chromatographic fractions are carefully monitored by HPLC, and only the fractions showing substantial purity are pooled. Desalting of the purified fractions independently checked for purity, is achieved using a gradient of $CH_3CN$ in 0.1% TFA. The center cut is then lyophilized to yield the desired peptide, the purity of which can be greater than 98%.

The synthesis is repeated using a chloromethylated resin to produce hpGRF(1–40)-OH using procedures as generally described in Rivier, J, *J. Amer. Chem. Soc.*, 96, 2986–2992 (1974).

EXAMPLE II

The synthesis of hpGRF(1–40)-[$Phe^{41}$, $Gln^{42}$]-$NH_2$ having the formula: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Glu-Ser-Asn-Gln-Glu-Arg-Gly-Ala-Phe-Gln-$NH_2$ is conducted in a stepwise manner using a Beckman 990 Peptide Synthesizer on an MBHA resin in the manner described in Example I. The peptide is judged to be substantially pure using TLC and HPLC.

EXAMPLE III

The synthesis of a hpGRF analog, i.e. hpGRF(1–40)-[$Phe^{41}$]-$NH_2$, having the formula: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Glu-Ser-Asn-Gln-Glu-Arg-Gly-Ala-Phe-$NH_2$ is conducted in a stepwise manner using a Beckman 990 Peptide Synthesizer on an MBHA resin, in the manner described in Example I. The peptide is judged to be substantially pure using TLC and HPLC.

The synthesis is repeated using a chloromethyleted resin to produce the same peptide in the free acid form as generally indicated hereinfore.

EXAMPLE IV

The synthesis of a hpGRF fragment, i.e. hpGRF(1–32) having the formula: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-$NH_2$ is conducted in a stepwise manner using a Beckman 990 Peptide Synthesizer on an MBHA resin in the manner described in Example I. This analog is judged to be substantially pure using TLC and HPLC.

EXAMPLE V

The synthesis of a hpGRF fragment i.e. hpGRF(1–27)-$NH_2$ having the formula: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-$NH_2$ is conducted in a stepwise manner using a Beckman 990 Peptide Synthesizer on an MBHA resin in the manner described in Example I. The peptide is judged to be substantially pure using TLC and HPLC.

EXAMPLE VI

The synthesis of a hpGRF fragment i.e. hpGRF(1–39)-$NH_2$, having the formula: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Glu-Ser-Asn-Gln-Glu-Arg-Gly-$NH_2$ is conducted in a stepwise manner using a Beckman 990 Peptide Synthesizer on an MBHA resin, in the manner described in Example I. The peptide is judged to be substantially pure using TLC and HPLC.

EXAMPLE VII

The synthesis of [$D-Ala^{15}$]-hpGRF(1–40) having the formula: H-Tyr-Ala-Asp-Ala-Ile-Phe-Thr-Asn-Ser-Tyr-Arg-Lys-Val-Leu-D-Ala-Gln-Leu-Ser-Ala-Arg-Lys-Leu-Leu-Gln-Asp-Ile-Met-Ser-Arg-Gln-Gln-Gly-Glu-Ser-Asn-Gln-Glu-Arg-Gly-Ala-$NH_2$ is conducted in a stepwise manner using a Beckman 990 Peptide Synthesizer on an MBHA resin in the manner described in Example I. The peptide is judged to be substantially pure using TLC and HPLC.

EXAMPLE VIII

The synthesis of a hpGRF fragment i.e. hpGRF(1–29) having the formula: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-$NH_2$ is conducted in a stepwise manner using a Beckman 990 Peptide Synthesizer on an MBHA resin in the manner described in Example I. The peptide is judged to be substantially pure using TLC and HPLC.

The synthesis is repeated using a chloromethylated resin to produce the same peptide in the free acid form as generally indicated hereinfore.

EXAMPLE IX

The synthesis of a hpGRF fragment i.e. hpGRF(1–28) having the formula: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-$NH_2$ is conducted in a stepwise manner using a Beckman 990 Peptide Synthesizer on an MBHA resin in the manner described in Example I. The peptide is judged to be substantially pure using TLC and HPLC.

The synthesis is repeated using a chloromethylated resin to produce the same peptide in the free acid form as generally indicated in Example I.

The two synthetic peptides prepared in Example I are compared with purified native hpGRF in in vitro assays and are found to exhibit similar potencies for the secretion of GH and similar intrinsic activities.

To determine the effectiveness of the various synthetic peptides to promote the release of growth hormone, in vitro assays are carried out using synthetic hpGRF of Example I as a standard in side-by-side comparison with equimolar concentrations of the various other analogs and fragments synthesized. Cultures are used which include cells of rat pituitary glands removed some four to five days previously. Cultures which are considered optimal for the secretion of growth hormone are used for the comparative testing, in the general manner described in Vale et al. Endocrinology, 91, 562-572 (1972). Incubation with the substance to be tested is carried out for 3 to 4 hours, and aliquots of the culture medium are removed and processed to measure their contents in immunoreactive GH(ir GH) by a well-characterized radioimmunoassay.

The results of this comparative testing for equimolar concentration are shown in Table I.

TABLE I

| Peptide | Comparison % |
| --- | --- |
| hpGRF(1–40)-NH$_2$ (standard for this test) | 100% |
| hpGRF(1–40)-OH | 100% |
| hpGRF(1–40)-[Phe$^{41}$, Gln$^{42}$]—NH$_2$ | 90% |
| hpGRF(1–40)-[Phe$^{41}$]—NH$_2$ | 110% |
| hpGRF(1–40)-[Phe$^{41}$]—OH | 60% |
| hpGRF(1–39)-NH$_2$ | 190% |
| hpGRF(1–32)-NH$_2$ | 110% |
| hpGRF(1–29)-NH$_2$ | 100% |
| hpGRF(1–29)-OH$_2$ | 40% |
| hpGRF(1–28)-NH$_2$ | <10% |
| hpGRF(1–27)-NH$_2$ | 15% |

In vitro testing of these synthetic peptides shows that the EC$_{50}$ varies from 20–100 picomolar and the lowest effective concentration to be 3–8 picomolar. The maximum effective concentration for hpGRF(1–40)NH$_2$ was 1 nanomolar.

In addition to the in vitro tests for secretion of growth hormone, in vivo experiments are also run by injecting the synthetic peptide through an indwelling catheter into freely running normal male rats. Animals are pretreated with FLA-63, a dopamine hydroxylase inhibitor that suppresses spontaneous GH secretion without affecting the response to exogenous GRF. Blood samples are taken through the same catheter immediately prior to and 5 and 20 minutes after injections; GH levels in blood are measured by radioimmunoassay. The results show that synthetic hpGRF(1–40)-NH$_2$ and other analogs are powerful stimulators of the secretion of pituitary GH. Dosages between about 40 nanograms and about 25 micrograms per Kg. of body weight were found to be effective.

Further testing shows that the synthetic hpGRF analog as synthesized in Example VII exhibits substantially the same potency as hpGRF(1–40)-NH$_2$.

Synthetic hpGRF should be useful for applications in which a physician wishes to elevate GH production. Stimulation of GH secretion by hpGRF and analogs is of interest in patients with complete or relative GH deficiency caused by underproduction of endogenous GRF. Furthermore, it is probable that increased GH secretion and its attendant increase in growth could be obtained in humans or animals with normal GH levels. Furthermore, hpGRF administration should alter body fat content and modify other GH-dependent metabolic, immunologic and developmental processes. For example, hpGRF may be useful as a means of stimulating anabolic processes in human beings under circumstances such as following the incurring of burns. In another example, hpGRF could be used in commercial animals, such as chickens, pigs, cattle and sheep, to accelerate growth and increase the ratio of protein to fat gained. For administration to humans, synthetic hpGRF peptides should have a purity of at least about 93% and preferably at least 98%. This purity means the intended peptide constitutes the stated weight % of all like peptides and peptide fragments present.

For the administration of synthetic hpGRF peptides to commercial and other animals in order to promote growth and reduce fat content, a purity as low as about 5%, or even as low as 0.1%, may be acceptable.

Synthetic hpGRF or the nontoxic salts thereof, combined with a pharmaceutically acceptable carrier to form a pharmaceutical composition, may be administered to animals, including humans, either intravenously, subcutaneously, intramuscularly, intranasally or even orally (at such time that effective couplers or carriers are developed). The administration may be employed by a physician to stimulate the release of GH where the host being treated requires such therapeutic treatment. The required dosage will vary with the particular condition being treated, with the severity of the condition and with the duration of desired treatment.

Such peptides are often administered in the form of pharmaceutically acceptable nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be orally administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered to humans under the guidance of a physician, and pharmaceutical compositions will usually contain the peptide in conjunction with a conventional, pharmaceutically-acceptable carrier. Usually, the parenteral dosage will be from about 40 nanograms to about 25 micrograms of the peptide per kilogram of the body weight of the host.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, modifications in the peptide chain, particularly deletions beginning at the carboxyl terminal of the peptide, can be made in accordance with the known experimental practises to date to create fragments that retain all or very substantial portions of the potency of the peptide, and such peptides are considered as being within the scope of the invention. Moreover, additions can be made to either terminal, or to both terminals, and/or generally equivalent residues can be substituted for naturally occurring residues, as is well-known in the overall art of peptide chemistry, to produce analogs having at least a substantial portion of the potency of the native polypeptide without deviating from the scope of the invention.

Various features of the invention are emphasized in the claims which follow.

What is claimed is:

1. A synthetic peptide having the formula: H-Tyr-Ala-Asp-Ala-Ile-Phe-Thr-Asn-Ser-Tyr-Arg-Lys-Val- Leu-D-Ala-Gln-Leu-Ser-Ala-Arg-Lys-Leu-Leu-Gln-Asp-Ile-Met-Ser-Arg-Gln-Gln-Gly-Glu-Ser-Asn-Gln-Glu-Arg-Gly-$R_{40}$-Y wherein $R_{40}$ is Ala or des-$R_{40}$, and Y signifies the carboxyl moiety of the amino acid residue at the C-terminal and is the radical —COOH or —CONH$_2$, or a fragment thereof extending from the N-terminus to a residue in position 28 through 39 which is biologically active to effect the release of GH from the pituitary, or a nontoxic salt thereof.

2. A synthetic peptide having the formula of claim 1 wherein Y is CONH$_2$.

3. A synthetic peptide having the formula of claim 1 wherein Y is COOH.

4. A synthetic peptide having the formula of claim 2 wherein $R_{40}$ is des-$R_{40}$.

5. A synthetic peptide having the formula of claim 2 wherein $R_{40}$ is Ala.

6. A pharmaceutical composition for stimulating the release of GH in an animal comprising an amount of the peptide of claim 1 or a nontoxic salt thereof effective to stimulate the release of GH from the pituitary, and a pharmaceutically acceptable liquid or solid carrier therefor.

7. A method of stimulating the release of growth hormone in an animal, which comprises administering to said animal an effective amount of a pharmaceutical composition as defined in claim 6.

8. A method in accordance with claim 7 wherein said administering is carried out either intravenously, subcutaneously, intramuscularly or intranasally.

9. A method of stimulating the release of GH in a mammal by administering an effective amount of a compound as defined in claim 2.

10. A method for accelerating the growth of nonhuman animals comprising administering an effective amount of a synthetic peptide defined by the formula:
H-Tyr-Ala-Asp-Ala-Ile-Phe-Thr-Asn-Ser-Tyr-Arg-Lys-Val-Leu-D-Ala-Gln-Glu-Ser-Ala-Arg-Lys-Leu-Leu-Gln-Asp-Ile-Met-Ser-Arg-$R_{30}$-$R_{31}$-$R_{32}$-NH$_2$
wherein $R_{30}$ is Gln or des-$R_{30}$, $R_{31}$ is Gln or des-$R_{31}$, $R_{32}$ is Gly or des-$R_{32}$, or a nontoxic salt thereof.

11. A method in accordance with claim 10 wherein $R_{28}$ is Ser and $R_{29}$ is Arg.

12. A method in accordance with claim 11 wherein $R_{30}$ is des-$R_{30}$, $R_{31}$ is des-$R_{31}$ and $R_{32}$ is des-$R_{32}$.

13. A method in accordance with claim 11 wherein $R_{30}$ is Gln, $R_{31}$ is Gln and $R_{32}$ is Gly.

* * * * *